United States Patent [19]

Carrieri et al.

[11] Patent Number: 5,631,469

[45] Date of Patent: May 20, 1997

[54] NEURAL NETWORK COMPUTING SYSTEM FOR PATTERN RECOGNITION OF THERMOLUMINESCENCE SIGNATURE SPECTRA AND CHEMICAL DEFENSE

[75] Inventors: Arthur H. Carrieri, Abingdon; Pascal I. Lim, Baltimore, both of Md.

[73] Assignee: The United States of America as represented by the Secretary of the Army, Washington, D.C.

[21] Appl. No.: 636,994

[22] Filed: Apr. 15, 1996

[51] Int. Cl.$^6$ .................................................... G01J 3/433
[52] U.S. Cl. ............................ 250/341.5; 250/341.6; 395/23
[58] Field of Search ................... 395/21, 23; 250/341.1, 250/341.5, 341.6

[56] References Cited

U.S. PATENT DOCUMENTS

| | | | |
|---|---|---|---|
| 5,241,179 | 8/1993 | Carrieri | 250/341 |
| 5,498,876 | 3/1996 | Moscovitch | 250/474.1 |
| 5,553,616 | 9/1996 | Ham et al. | 128/633 |
| 5,572,028 | 11/1996 | Moscovitch et al. | 250/337 |

OTHER PUBLICATIONS

A.H. Carrieri, "Infrared Detection of Liquids on Terrestrial Surfaces by $CO_2$ Laser Heating," Appl. Opt., 29(33), 4907–4914, 1990 no date.

H.F. Hameka and J.O. Jensen, "Theoretical Prediciton of the Infrared and Raman Spectra of O–ethyl S–2diisopropyl amino ethyl eethyl phosphonothiolate," Int. J. Quant. Chem., (vol. 50), 161–172, 1994 no month.

A.H. Carrieri and Pascal I.Lim, "Neural Network Pattern Recognition of Thermal–Signature Spectra for Chemical Defense" Appl. Optics, vol.34 No. 15 2623–2635 (1995) no month.

*Primary Examiner*—David P. Porta
*Assistant Examiner*—David Vernon Bruce
*Attorney, Agent, or Firm*—Ulysses John Biffoni

[57] ABSTRACT

A four-layer neural network is trained with data of midinfrared absorption by nerve and blister agent compounds (and simulants of this chemical group) in a standoff detection application. Known infrared absorption spectra by these analyte compounds and their computed first derivative are scaled and then transformed into binary or decimal arrays for network training by a backward-error-propagation (BEP) algorithm with gradient descent paradigm. The neural network transfer function gain and learning rate are adjusted on occasion per training session so that a global minimum in final epoch convergence is attained. Three successful neural network filters have been built around an architecture design containing: (1) an input layer of 350 neurons, one neuron per absorption intensity spanning $700 \leq v \leq 1400$ wavenumbers with resolution $\Delta v=2$; (2) two hidden layers in 256- and 128-neuron groups, respectively, providing good training convergence and adaptable for downloading to a configured group of neural IC chips; and (3) an output layer of one neuron per analyte—each analyte defined by a singular vector in the training data set. Such a neural network is preferably implemented with a network of known microprocessor chips.

19 Claims, 3 Drawing Sheets

NEURAL NETWORK COMPUTING SYSTEM FOR PATTERN RECOGNITION OF THERMOLUMINESCENCE SIGNATURE SPECTRA AND CHEMICAL DEFENSE

The invention described herein may be manufactured, used or licensed by or for the government.

FIELD OF THE INVENTION

The present invention is related to the use of a neural network computing system recognizing the thermoluminescence signature spectra of chemical compounds and finds particular utility in the recognition of nerve and blister agent compounds.

DESCRIPTION OF THE PRIOR ART

The prior art related to the present application includes the following references, whose disclosures are hereby incorporated by reference in their entireties into this specification:

A. H. Carrieri, "Infrared Detection of Liquids on Terrestrial Surfaces by $CO_2$ Laser Heating," *Appl. Opt.*, 29(33), 4907–4913, 1990.

The neural network proposed is a device that will integrate to a system similar to the one disclosed in this publication.

A. H. Carrieri, "Thermoluminescence Sensor for the Remote Detection of Chemical Agents and Their Simulants," U.S. Pat. No. 5,241,179, assigned to the U.S.A as represented by the Secretary of the Navy, 31 August 1993.

This U.S. patent discloses a Thermoluminescence (TL) system. The neural network of the present invention will perform the signal processing of this TL sensor and similar systems.

H. F. Hameka, and J. O. Jensen, "Theoretical Prediction of the Infrared and Raman Spectra of O-ethyl S-2diisopropyl amino ethyl methyl phosphonothiolate," *Int. J. Quant. Chem.*, accepted for publication February 1994.

FIG. 1 of the present application is taken from this publication with permission of the authors.

M. Rrisch, J. Foresman, and A. Frisch, *Gaussian 92 User's Guide*, Gaussian, Inc., © 1992.

This is the handbook of the quantum mechanics molecular orbital code for predicting spectra and is used to illustrate how the network performance of the present invention compares against theoretical predictions.

SUMMARY OF THE INVENTION

An object of the invention is to provide a system and method for recognizing chemical compounds on the basis of their thermoluminescence signature spectra.

To this and other objects, the invention is directed to a system and method in which data of midinfrared absorption by nerve and blister agent compounds (and simulants of this chemical group) are used as features for training 4-layer neural networks in a standoff detection application. Known infrared absorption spectra of these analyte compounds and their computed first derivative are scaled and then transformed into binary or decimal arrays for network training by a backward-error-propagation (BEP) algorithm with gradient descent paradigm. The neural network transfer function gain and learning rate are adjusted on occasion per training session so that a global minimum in final epoch convergence is attained.

Three successful neural network filters have been built around an architecture design containing: (1) an input layer of 350 neurons, one neuron per absorption intensity spanning $700 \leq v \leq 1400$ wavenumbers with resolution $\Delta v=2$; (2) two hidden layers in 256- and 128-neuron groups, respectively, providing good training convergence and adaptable for down-loading to a configured group of neural IC chips; and (3) an output layer of one neuron per analyte— each analyte defined by a singular vector in the training data set.

A weight matrix per filter yielding best performance by software simulation is transferred to a neural network which in a preferred embodiment includes eight interconnected INTEL 80170NX Electronically Trainable Analog Neural Network (ETANN) chips, housed arid connected on a mother circuit board, for real-time testing of external streams of data. These test data include infrared training spectra with added noise, spectral predictions by theoretical model, or preprocessed spectra from a sensor unit. Detection features in data forwarded to the network filters are imprints of molecular vibrational modes by nine analyte compounds. Preprocessing of raw spectra involves digitization of interferograms and fast Fourier transformation, spectrum subtraction, spectrum normalization and baseline correction, electronic noise filtration, and polarity adjustment of enhanced emission bands brought on by the sensor's irradiating beam source.

These neural network pattern recognition systems can achieve in situ spectral discrimination of organic liquid layers on the ground and their evaporated vapor clouds when integrated into a mobile thermoluminescence field sensor.

BRIEF DESCRIPTION OF THE DRAWINGS

The preferred embodiment of the invention will now be described in detail with reference to the drawings, in which.

DETAILED DESCRIPTION OF THE PREFERRED EMBODIMENT

Figure 1:
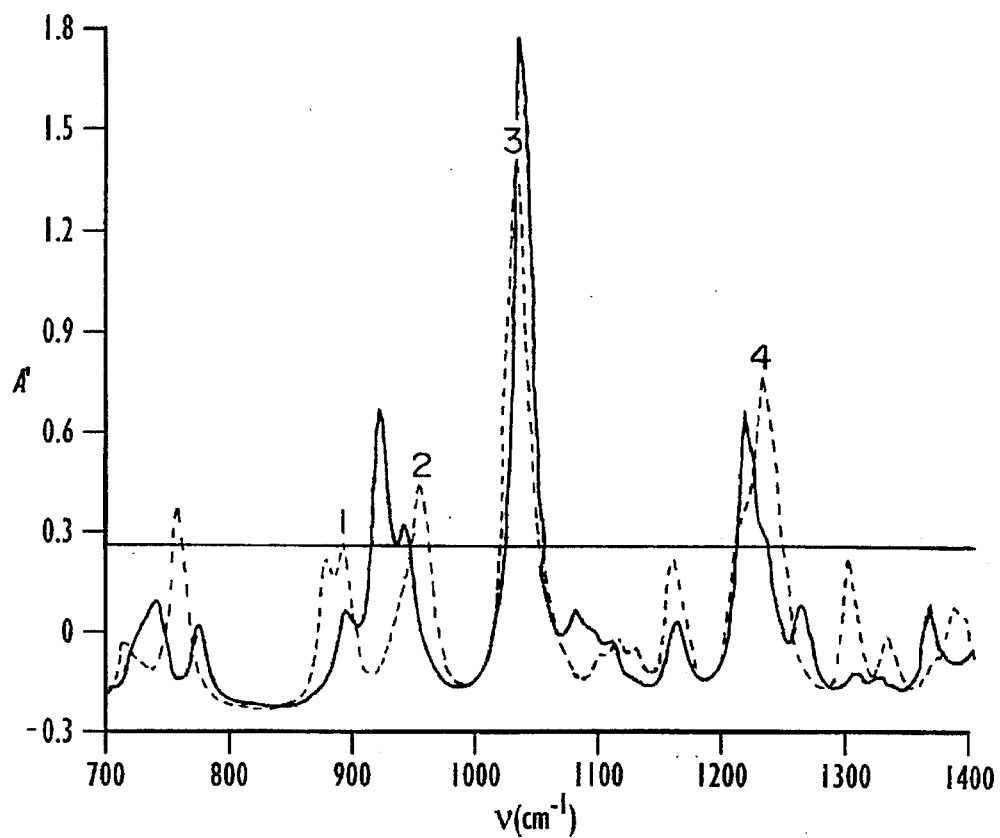
FIG. 1 shows a scaled infrared absorption spectrum of the liquid chemical nerve agent Ethyl S-(2-Diisopropylaminoethyl) Methylphosphonothiolate (VX)
Figure 2:
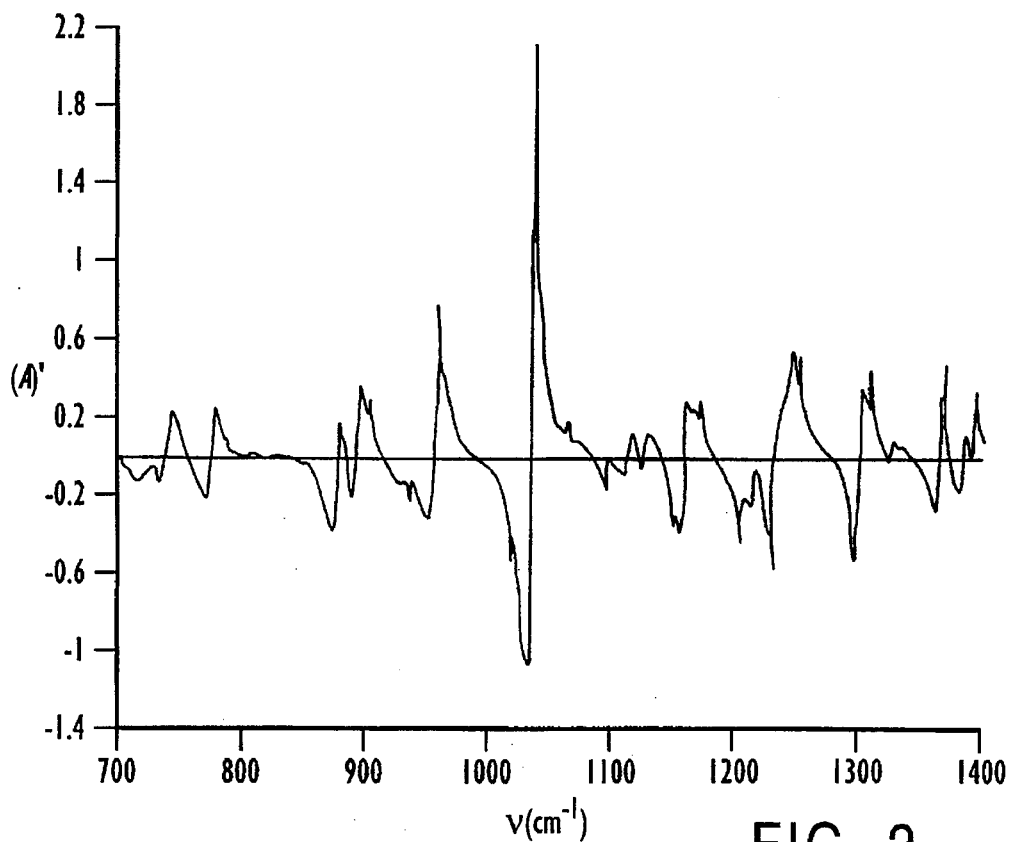
FIG. 2 shows a first-derivative scaled infrared absorption spectrum of the liquid chemical nerve agent Ethyl S-(2-Diisopropylaminoethyl) Methylphosphonothiolate (VX) of FIG. 1.

The preferred embodiment of the invention is directed to a Neural Network Computing (NNC) system for detecting surface chemical contamination by thermoluminescence. Features for the radiometric detection of the contaminant compound (analyte), or group of compounds, are absorption and emission moieties carried in a thermal energy release by the surface of the compound vis-à-vis stimulation by an irradiating beam source. Conversion of the incident beam single energy (energy efficiently absorbed into the material volume of the compound, and usually selected outside the detection band of the measuring instrument) to a broad thermal release over the surface boundary of the compound under irradiation is called thermoluminescence.

The irradiated zone builds in temperature ($T_{surf}$) resulting in a shift in graybody emissions liberated by the material toward higher infrared (IR) energies. When this Planck distribution spectrum shifts at maximum rate, i.e., when ($T_{surf}$) passes through 0 (the dot symbol denotes differentiation with respect to beam irradiation time), the surface is in its most thermally dynamic state while emissivity of the infrared-active analyte and background medium are at their highest contrast. Contaminant molecules excited into their fundamental vibrational modes, within this graybody spectrum, will show their band structure prominently by a simple spectrum subtraction about an irradiation period where $\dot{M}_{\lambda_m}'$ is maximum, $\dot{M}_{\lambda_m}$ being the peak value if of the thermal graybody emissions.

A functional and practical field sensor built around this principle will include a system whose optics, electronics, algorithms, and neural network pattern matching computations will do a full range of TL detection tasks as stated. Electronic and mathematical data handling operations necessary to determine an in situ presence or absence of various analyte compounds include: (1) A/D data acquisitions from a Michelson interferometer for generating a plurality of temporal radiance patterns by IR interference (interferograms), (2) fast Fourier transformation (FFT) of the interferograms for frequency (energy) deconvolution of the collected radiance, (3) spectrum subtraction, baseline correction, and positive polarity adjustment of bands for resolving the contaminant's molecular vibrational modes, (4) spectrum z-scaling for normalization of IR spectra, (5) noise filtration, (6) neural network computing for pattern recognition of the analyte's vibrational spectrum, (7) mapping coordinates for contaminant locations through a Global Positioning System, and a variety of systems-related data routing and automation operations with safety checks and feedback functions. The present invention is directed to the neural network computing component of such a system.

The inventors will describe the preferred embodiment of the invention in the following manner. First, the inventors will briefly review neural network computing and design then build three simplistic spectral pattern-matching filters in binary absorption, decimal absorption, and decimal derivative-absorption training data formats. Subsequently, network training procedures to recognize a group of nine analyte compounds are presented, followed by test procedures using noisy training data, theoretical predictions of spectra, and sensor data. The effects of noise on network pattern-matching performance will be examined, and a down-loading procedure of trained network architecture and weight matrix filter to semiconductor hardware for full network integration into a thermoluminescence (TL) sensor data acquisition system will be set forth. Finally, the inventors will suggest improvements in quantum mechanics spectral computation methods that should improve the precision of predicting vibrational energy states in these analyte molecules (fed through these neural networks), discuss an alternate network paradigm and hardware support for possible improved confidence of detection, and finally, summarize the goals of the invention.

Neural network systems designed to interpret infrared spectra are successful and usefull laboratory devices. Certain advantages of these systems are realized over statistical model linear regression approaches of spectral discrimination: Neural networks use nonlinear transform functions to map nonlinear variables, they can operate on non-normal distributions of data, and input data need not be linearly independent (orthogonal input vector space). Such circumstances are encountered in recognizing patterns of thermal activity in organics; for example, the preferred embodiment of the present invention is concerned with absorption and emission rates from liquid and vapor organophosphonate contaminants brought out by a controlled beam stimulation of TL. To accomplish a Neural Network Computing (NNC) system for this TL standoff detection problem, the preferred embodiment uses software called DynaMind (a product of NeuroDynamX, Inc) and hardware with accessories for configuring and testing eight Intel 80170NX Electronically Trainable Neural Network (ETANN) chips (a product of Intel, Inc). However, those skilled in the art who have reviewed this specification will readily appreciate that the present invention is not limited to any particular brand of software or hardware. The software and hardware products named are compatible, so that NNCs developed in software simulation are easily downloaded to a configured and connected hardware board.

A brief explanation of some terminology and function is in order before these networks are disclosed. Neural networks are neurons or processing elements (PEs) grouped in input, hidden, and output layers that communicate in parallel via full interconnections of PEs between layers. The strengths of interconnections are called weights. In training sessions of a network, learning is composed by a training algorithm and paradigm, causing pattern updated adjustments in weight strengths. The training algorithm used here is called Backward-Error Propagation (BEP), a method of error analysis where perturbations put on the weights are distributed in a manner to reduce overall network epoch error. All weights of the network are dimensions in the domain of the BEP transform (weight space). The learning paradigm (convergence to a correct result) uses a gradient descent method for seeking global minima in this weight-dimensional space.

Each of the first hidden layer PEs sums the product of each preceding input layer PE signal and its respective weight (plus bias weight, if present) and passes this value to a transfer function (TF) that scales all summed inputs to yield new signals conducted to a neuron in the succeeding hidden layer or output layer (feed-forward topology). The TF used here is of a hyperbolic tangent form (tanh) with limits of ±1 for scaling all incoming PE signals, within these limits, and an adjustable transfer function gain for controlling the TF rate of change, also between these limits; both parameters control conduction of PE output (firing of neuron). This tanh function is useful when training sets of nonuniformly distributed data with densities away from the set mean value, as is typical of IR spectra of organic compounds (sometimes referred to as the fingerprint energy band).

The network topology is disorganized before training; neural pathways are randomized with no associative learning. Training data consist of nine sets of standard absorption spectra together with a singular vector representation per analyte called the target output. The goal of the network is to associate each class of vibrational bands (uncommon feature of each molecular species) to its defined vector representation by the BEP mapping. Learning by the network is complete when error in this transformation is null, i.e. zero, the network converges yielding a global minimum on the topological weight surface via gradient descent. In gradient descent, this topological surface in weight space is reformed, gradually in training time (weight updates), as network rms error per epoch decreases $$\left( E = 1/2 \sum_{i=0}^{9} |\text{Network}_i - \text{Target}_i|^2 \right)$$

with respect to the weight matrix $$(W): \delta W = -\alpha \frac{\partial E}{\partial W}.$$

The proportionality constant $\alpha$ is called the network learning rate.

This prototype TL sensor uses a scanning Michelson interferometer for generating a plurality of temporal voltage The molecular structure of nerve agent Ethyl S-(2-Diisopropylaminoethyl) Methylphosphonothiolate (VX), includes bond angles and lengths that were computed by a geometry optimization option in a quantum mechanics program called Gaussian 92. This compound is the first of seven analyte compounds whose experimentally measured vibrational spectrum in part form the training basis set of these networks. Table 1 at the end of this paragraph lists energies of the strongest vibrational transitions and mode assignments in VX and six other analyte compounds of the network training data set. The strongest vibrational modes in each molecular species represent singular classes of detection features. (The dipole moment derivative quantity between a bonded atom pair in the molecule is responsible for the IR band and its strength of transition.)

TABLE 1

| Analyte Nomenclature (II) # | Formula | Band | Vibrational Energy ($cm^{-1}$) | Scaled Absorption Intensity | Mode Assignment |
|---|---|---|---|---|---|
| VX(0) ethyl(2diisopropylaminoethyl) Methyl-phosphonothiolate | $CH_3CH_2OP(O)$— —$(CH_3SCH_2CH_2N(CH(CH_3)_2)_2$ | 1 | 894 | 0.2498 | P2—$C_6H_3$ rock |
| | | 2 | 956 | 0.4380 | $C3H_2$ bend |
| | | 3 | 1036 | 1.3941 | P2-O5-C10 stretch |
| | | 4 | 1230 | 0.7388 | $C3H_2$ bend |
| DIMP(2) diisopropylmethyl-phosphonate | $OP(OCH(CH_3)_2)_2CH_3$ | 1 | 984 | 0.8883 | C—O—P—O—C stretch |
| | | 2 | 1012 | 0.6748 | C—O—P—O—C stretch |
| | | 3 | 1110 | 0.2483 | O—$C_3$ stretch |
| | | 4 | 1244 | 0.6149 | P=O stretch |
| MMP(3) dimethylmethyl-phosphonate | $OP(OCH_3)_2CH_3$ | 1 | 820 | 0.3010 | P—C stretch |
| | | 2 | 1032 | 1.2025 | C—O—P—O—C stretch |
| | | 3 | 1058 | 0.6389 | C—O—P—O—C stretch |
| | | 4 | 1246 | 0.5877 | P=O stretch |
| GA(4)-Tabun ethyl n-dimethyl-phosphoramido-cyanidate | $C_2H_5OP(O)(CN)N(CH_3)_2$ | 1 | 1006 | 0.8612 | P—O—C stretch |
| | | 2 | 1030 | 0.7716 | C—N—C bend |
| | | 3 | 1268 | 0.7235 | P=O stretch |
| | | 4 | 1320 | 0.4208 | N—C stretch |
| GB(5)-Sarin iospropylmethyl-phosphonofluoridate | $CH_3P(O)(F)O(iC_3H_7)$ | 1 | 838 | 0.3174 | P—F stretch |
| | | 2 | 1014 | 1.1719 | P—O stretch |
| | | 3 | 1278 | 0.6790 | P=O stretch |
| | | 4 | 1320 | 0.3486 | C—H bend |
| GD(6)-Soman methyl 1-methyl-2-dimethylpropyl-phosphonofluoridate | $CH_3P(O)(F)O(CH_3)$— —$CHC(CH_3)_3$ | 1 | 986 | 0.4235 | $C_bH_3$ rock |
| | | 2 | 1000 | 0.4557 | P—O stretch |
| | | 3 | 1018 | 1.1152 | P—O stretch |
| | | 4 | 1284 | 0.7892 | P=O stretch |
| SF96(8) polydimethylsiloxane | $[-Si(CH_3)_2O-]_n$ | 1 | 800 | 0.7581 | Si—$CH_3$ rock |
| | | 2 | 1022 | 0.5513 | Si—O—Si stretch |
| | | 3 | 1094 | 0.5388 | Si—O—Si stretch |
| | | 4 | 1262 | 0.6088 | Si—$CH_3$ sym stretch | waveforms called interferograms (time-dependent intensity patterns of constructive and destructive interference in collected IR waves). The interferograms data rate is dictated by a period of constant velocity movement in the interferometer's oscillating mirror. Measurement of the interferograms is done by amplifying, digitizing, and storing signal output from a cooled MCT detector chip located in the optical path after the interferometer and in the focus of the incident TL radiance. This interferogram is transformed into IR frequency amplitudes by an on-board fast Fourier transform (FFT) algorithm (part of the sensor array-processor data acquisition and preparation unit). Contiguous sets of spectra are subtracted in a period of beam irradiation causing a developing thermal gradient in the sample to maximize. These difference FFT intensities are preprocessed then configured into binary or direct analog arrays of data covering $700 \leq v \leq 1400$ wavenumbers (wn's) in 2 wn resolution, buffered, the n sent to the neural network input layer (350 simultaneous intensities of spectral data).

Training and testing data representations in this NNC system take on three separate structures. For example, the binary structure from the spectrum of VX shown with the solid line in FIG. 1 was produced from experimental measurement of neat liquid VX by a Nicolet 10-DX FTIR instrument.

FIG. 1 shows a scaled infrared absorption spectrum of the liquid chemical nerve agent Ethyl-(2-Diisopropylaminoethyl) Methylphosphonothiolate (VX). The dashed curve is a theoretical prediction. The solid curve is an experimental measurement where numbers above the peaks identify four key vibrational modes in the VX molecule. The horizontal line A'=0.2498 corresponds to the 4th strongest vibrational intensity; a binary divider of this spectrum: binary+1 for A'$\geq$0.2498 and binary −1 for A'<0.2498. Training data are of a 25×14 binary matrix form:

| | | | | | | | | | | | | | | |
|---|---|---|---|---|---|---|---|---|---|---|---|---|---|---|
| -1 | -1 | -1 | -1 | -1 | -1 | -1 | -1 | -1 | -1 | -1 | -1 | -1 | -1 | -1 |
| -1 | -1 | -1 | -1 | -1 | -1 | -1 | -1 | -1 | -1 | -1 | -1 | -1 | -1 | 1 |
| -1 | -1 | -1 | -1 | -1 | -1 | -1 | -1 | -1 | -1 | -1 | -1 | -1 | -1 | 1 |
| -1 | -1 | -1 | -1 | -1 | -1 | -1 | -1 | -1 | -1 | -1 | -1 | -1 | -1 | 1 |
| -1 | -1 | -1 | -1 | -1 | -1 | -1 | -1 | -1 | -1 | -1 | -1 | -1 | -1 | 1 |
| -1 | -1 | -1 | -1 | -1 | -1 | -1 | -1 | -1 | -1 | -1 | -1 | 1 | -1 | 1 |
| -1 | -1 | -1 | -1 | -1 | -1 | -1 | -1 | -1 | -1 | -1 | -1 | -1 | -1 | 1 |
| -1 | -1 | -1 | -1 | -1 | -1 | -1 | -1 | -1 | -1 | -1 | -1 | 1 | 1 | 1 |
| 1 | 1 | 1 | 1 | 1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | 1 | 1 | 1 | 1 | 1 | 1 | 1 | 1 | |
| 1 | 1 | 1 | 1 | 1 | 1 | 1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | 1 | -1 | |
| -1 | -1 | 1 | 1 | 1 | 1 | 1 | 1 | 1 | 1 | 1 | 1 | 1 | 1 | |
| 1 | 1 | 1 | 1 | 1 | 1 | 1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | | | | | | | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |
| -1 | -1 | -1 | -1 | -1 | -1 | -1 | -1 | -1 | -1 | -1 | -1 | -1 | -1 | |

The array bits are separated by 2 $cm^{-1}$, read left-to-right by row (element [1,1] is binary A' (702) ... element [25,14] is binary A' (1400)). The right-most column is a vector associating this map to VX. This binary matrix makes up one training set exemplar. A variety of mathematical operations are performed on raw data (stored laboratory spectra) to produce this; exemplar. They include scaling by the set expression $$A' = \left\{ \frac{A_i - \langle A \rangle}{4s} \right\},$$

where brackets denote mean value, the subscript denotes IR absorption frequency (PE number 0 . . . 349 of the network input layer), and s is the standard deviation. This will standardize the intensity scale of spectra read in from different spectrometer systems, i.e., it allows a common ordinate axis for the network training data set and incoming sensor data sets. It also provides a range of spectral amplitudes compatible to the tanh transfer function limits set in the network semiconductor hardware. The next preprocessing operation applies a noise reduction filter the scaled spectra if extraneous signal is present. Savitzky-Golay type digital smoothing polynomial filters achieve limited success for this operation. The scaled and smoothed spectrum is next prepared for binary encoding. Binary values are grouped by first locating the forth-strongest absorption peak intensity in each spectrum. A +(−)1 bit is assigned to each datum of the scaled spectrum whose intensity lies at or above (below) the 4th-peak intensity divisor. The reason for locating the fourth-peak intensity is that, within the bandwidth of the TL sensor, the quantity of strong vibrational states in these analyte molecules do not usually exceed four. The bottom of FIG. 1 shows the resultant 25×14 binary field with a singular 9-dimensional vector (one dimension per training set exemplar in the training data block) in the right-most column to associate this binary field to the chemical agent VX.

When detecting multiple contaminants, the network binary filter must recognize groups of spectrum bands per analyte in constant intensity proportion. A preprocessing algorithm that cascades binary data fields is used for this task. The procedure first involves submission and forwarding of the fourth-peak binary field (FIG. 1) to the trained network. The network is next checked for a positive identification. If that check is negative, the algorithm continues on locating a fifth peak and, if present, generates a new binary field where the binary divider correlates to this scaled fifth-absorption bandhead. The algorithm continues seeking peaks and submitting binary files to the network until an offset peak intensity is reached—an intensity set above the noise level of the spectrometer instrument.

The second data structure uses the same 25×14 matrix format as with the binary field except here the absorption spectra, in a string of decimal data points, are written directly into the matrix after D/A conversion of the preprocessed FFT. This decimal method is more direct, less time consuming, and slightly more precise than that of the binary method of training and feed-forwarding to the NNC. However, hardware is now more complex and the data acquisition system more bulky and difficult to calibrate since the spectrometer electronics (a digital data acquiring instrument) must now include multiplexed A/D converters with 350 channels, once channel per input PE.

The last data structure designed, built, and evaluated for training by this same network architecture is identical to the above absorption structure, except a differentiating operation is added after FFT subtraction and preprocessing operations. The goal was to increase network specificity of detection by applying the energy derivative $$\frac{\partial A}{\partial v}$$

operator just before submission. of the spectrum to the network, especially where overlapping band structure is present. The inventors' experience in testing neural networks with derivative-based spectra suggests that prefiltering and smoothing operations are necessary and require special handling in preprocessing, since noise by the instrument can cause substantial error peaks in A' (about abrupt adjacent data points).

FIG. 2 shows the smoothed derivative absorption training spectrum of FIG. 1, with its decimal training data set representation.

These network training data are of a 25×14 decimal matrix form shown below. The array numerics are spearted by 2 cm$^{-1}$, read left-to-right by row (element [1,1] is decimal A' (702) . . . element [25,14] is decimal A' (1400)). The right-most column is a vector associating this map to VX.

network net file. Weights are initialized before training the network, and a filter function is used during training sessions to accept only those weight values between ±2.5, the allow-

| | | | | | | | | | | | | | | |
|---|---|---|---|---|---|---|---|---|---|---|---|---|---|---|
| 0.068 | 0.035 | −0.000 | −0.062 | −0.060 | −0.085 | −0.102 | −0.118 | −0.123 | −0.120 | −0.115 | −0.097 | −0.082 | −0.067 | −1 |
| −0.047 | −0.050 | −0.065 | −0.087 | −0.074 | −0.037 | 0.055 | 0.153 | 0.236 | 0.258 | 0.221 | 0.165 | 0.112 | 0.067 | 1 |
| 0.037 | 0.009 | −0.040 | −0.055 | −0.090 | −0.135 | −0.187 | −0.225 | −0.192 | −0.057 | 0.105 | 0.218 | 0.246 | 0.210 | 1 |
| 0.150 | 0.100 | 0.063 | 0.039 | 0.032 | 0.029 | 0.027 | 0.022 | 0.015 | 0.007 | −0.000 | 0.002 | 0.007 | 0.017 | 1 |
| 0.014 | 0.015 | 0.012 | 0.005 | 0.007 | 0.000 | 0.002 | −0.000 | −0.000 | −0.005 | −0.002 | −0.000 | 0.002 | −0.000 | 1 |
| 0.000 | −0.002 | −0.009 | −0.014 | −0.017 | −0.020 | −0.020 | −0.027 | −0.025 | −0.045 | −0.069 | −0.100 | −0.143 | −0.198 | 1 |
| −0.263 | −0.340 | −0.386 | −0.368 | −0.220 | −0.014 | 0.127 | 0.107 | 0.017 | −0.120 | −0.205 | −0.138 | 0.067 | 0.290 | 1 |
| 0.374 | 0.354 | 0.300 | −0.230 | 0.309 | 0.098 | 0.058 | 0.034 | 0.014 | −0.002 | −0.027 | −0.052 | −0.082 | −0.107 | 1 |
| −0.127 | −0.137 | −0.137 | −0.128 | −0.117 | −0.109 | −0.120 | −0.135 | −0.163 | −0.200 | −0.242 | −0.286 | −0.310 | −0.285 | 1 |
| −0.180 | 0.010 | 0.216 | 0.782 | 0.436 | 0.414 | 0.373 | 0.308 | 0.236 | 0.180 | 0.135 | 0.102 | 0.070 | 0.049 | |
| 0.034 | 0.022 | 0.014 | 0.009 | −0.002 | −0.009 | −0.015 | −0.024 | −0.029 | −0.039 | −0.052 | −0.065 | −0.082 | −0.107 | |
| −0.140 | −0.170 | −0.198 | −0.227 | −0.335 | −0.443 | −0.566 | −0.697 | −0.833 | −0.973 | −1.084 | −1.098 | −0.827 | 0.181 | |
| 1.056 | 1.104 | 0.945 | 0.808 | 0.640 | 0.494 | 0.388 | 0.306 | 0.233 | 0.172 | 0.143 | 0.137 | 0.135 | 0.118 | |
| 0.185 | 0.080 | 0.083 | 0.088 | 0.083 | 0.072 | 0.055 | 0.039 | 0.020 | 0.007 | −0.007 | −0.025 | −0.047 | −0.074 | |
| −0.097 | −0.168 | −0.025 | 0.012 | 0.019 | −0.004 | −0.030 | −0.042 | −0.069 | −0.094 | −0.030 | 0.080 | 0.113 | 0.067 | |
| −0.019 | −0.062 | −0.057 | 0.020 | 0.107 | 0.128 | 0.102 | 0.065 | 0.030 | 0.002 | −0.027 | −0.057 | −0.099 | −0.147 | |
| −0.250 | −0.330 | −0.386 | −0.341 | −0.102 | 0.177 | 0.280 | 0.245 | 0.215 | 0.225 | 0.225 | 0.196 | 0.281 | 0.090 | |
| 0.055 | 0.029 | 0.007 | −0.012 | −0.027 | −0.044 | −0.067 | −0.099 | −0.138 | −0.190 | −0.238 | −0.261 | −0.256 | −0.220 | |
| −0.217 | −0.246 | −0.258 | −0.192 | −0.087 | −0.060 | −0.120 | −0.223 | −0.328 | −0.399 | −0.414 | −0.584 | −0.019 | 0.153 | |
| 0.233 | 0.230 | 0.251 | 0.318 | 0.434 | 0.522 | 0.532 | 0.466 | 0.379 | 0.301 | 0.210 | 0.163 | 0.127 | 0.097 | |
| 0.075 | 0.057 | 0.047 | 0.037 | 0.027 | 0.020 | 0.012 | 0.005 | −0.004 | −0.015 | −0.029 | −0.065 | −0.104 | −0.170 | |
| −0.271 | −0.409 | −0.544 | −0.396 | 0.032 | 0.251 | 0.306 | 0.314 | 0.286 | 0.243 | 0.158 | 0.098 | 0.058 | 0.032 | |
| −0.004 | −0.032 | −0.027 | 0.009 | 0.053 | 0.055 | 0.030 | 0.030 | 0.042 | 0.034 | 0.019 | 0.012 | −0.004 | −0.019 | |
| −0.039 | −0.067 | −0.084 | 0.097 | −0.135 | −0.198 | −0.265 | −0.293 | −0.172 | 0.123 | 0.305 | 0.462 | 0.077 | −0.049 | |
| −0.137 | −0.170 | −0.175 | −0.185 | −0.102 | 0.055 | 0.093 | 0.024 | 0.019 | 0.112 | 0.193 | 0.167 | 0.112 | 0.062 | |

Training each network to its data structure is done by use of the DynaMind software product, BEP training algorithm option with gradient descent paradigm. Each preprocessed data structure is loaded on computer file with a suffix io; that file contains a header block with quantity input and output layer PEs and comment information. Input, hidden, and output layer PEs are keyed into the program per network file name and description. The input layer is a 350 dimensional space, and quantity of PEs in the output layer is nine, or one neuron per analyte contained in the training data set.

Network hidden layers and PEs per layer were determined through trial-and-error training experiments in software simulation. Starting with a single hidden layer of 175 PEs, rates of network convergence and final epoch error were checked by observing the rms error instrument brought on screen during training sessions. Since the weight matrices developed after network training are basic spectral look-up tables, and the input space is one running variable in energy, rms error was chosen as the key network performance parameter of training. An increase of hidden layer PEs from 175 to 550 (experiments were done in steps of about 100 PEs) produced the best single hidden layer network performance result. For IC hardware compliance reasons, this was changed to a modularized 2-hidden layer architecture of 256 and 128 successive groups of PEs. (Reducing network complexity by pruning hidden layer PEs that do not contribute to performance, thereby increasing network throughput, is not a current option in the version of Dyna-Mind code used.)

Intel's 80170NX ETANN chip architecture, onto where the network weight matrix is down-loaded, is restricted to a maximum of 64 PEs per hidden and output layers and 128 PEs input layer mode, and the quantity of chips on one bus (EMB printed circuit board) is limited to eight. It will be explained below how the above four-layer network architecture (one input, two hidden, one output) meets the hardware constraint when the trained weight matrix is modularized and implemented onto eight interconnected Intel 80170NX IC chips. The network tanh TF limits, learning rate, and gain parameters are next programmed to create a able range for the ETANN chips. The steps per training epoch are fixed at nine, or one sweep of neurons in the network output layer.

The DynaMind executable now has all necessary information for start-up of a training session, or a resume of training. Training sessions are periodically interrupted to change learning rate and TF gain parameters, then re-started, to minimize epoch error when producing these fine-tuned weight matrices (filters) by absorption-binary, absorption-decimal, and derivative-absorption-decimal structured data formats. Epoch errors below $10^{-15}$ were attained in final training convergence by all three network training structures using this method of parameter adjustment for seeking, centering, and settling to the global minimum.

On completion of training, DynaMind writes the four-layer network weight matrix result into a network.net file; each nine-analyte pattern matching filter occupies about 1 MB of computer RAM memory per data structure and network architecture previously discussed. Pattern recognition from a stream of external spectral data, in forms of preprocessed sensor, theoretical prediction, or manipulated training data sets is started by first loading the network.net and data.io files into CPU memory, linkage, then CPU access to the program executable via a mouse click-on maneuver of a network file called net.set. The network of the fourth-peak binary structure was tested first, and the results are shown in Table 2 below.

TABLE 2

| Binary Data Set Representation | | Noise Added (%) | Correct Identification Agent (% True) | Incorrect Identification Agent (% False) |
|---|---|---|---|---|
| Training Spectrum | Testing Spectrum | | | |
| $\sum_{i=0}^{8} A_i^B$ | $A_0^B, A_1^B, A_2^B$ $A_3^B, A_4^B, A_5^B$ $A_6^B, A_7^B, A_8^B$ | 15 | 0(98.7), 1(98.7), 2(98.7) 3(98.7), 4(98.7), 5(98.7) | None None None |
| | $A_0^B, A_1^B, A_2^B$ $A_3^B, A_4^B, A_5^B$ $A_6^B, A_7^B, A_8^B$ | 20 | 6(98.7), 7(98.7), 8(98.7) 0(98.7), 1(98.7), 2(98.7) 3(98.7), 4(98.7), 5(98.7) 6(97.9), 7(98.7), 8(98.7) | None None $8 \rightarrow$ 5(89.4) |
| $\sum_{i=0}^{8} A_i^B$ | $T_0^B$ $T_3^B$ $T_4^B$ $T_5^B$ $T_6^B$ | 0 | No ID No ID No ID No ID 6(90.0) | None None None 6(98.4) 2(98.7) |
| $\sum_{i=0}^{8} A_i^B$ | $S_2^B$ $S_3^B$ $S_8^B$ | 0 | 2(98.7) 3(98.7) 8(98.7) | None None None |

Binary Divider is the intensity of the 4th strongest peak per scaled absorption spectrum.
Input layer neurons = 350, 1st hidden layer neurons = 256 and 2nd hidden layer neurons = 128, output layer neurons = 9, epoch error < $10^{-15}$, $A^B$ = binary IR absorption spectrum (Nicolet 10-DX spectrometer measurement), i = (0, 1, 2, 3, 4, 5, 6, 7, 8) ≡ (VX, Vx, DIMP, DMMP, GA GB, GD, GF, SF96), $T^B$ = binary Gaussian 90 model theoretical prediction spectrum, $S^B$ = binary interferometer sensor spectrum. Final Transfer Function teaming Rate/Gain = 0.010/2.00, sigmoid limits = ±1, and weight filter = ±2.5

Given are network neurons per input-hidden-output layers, converged epoch error, and tanh transfer function parameters including gain and learning rate. The summed A-symbol suggests a binary format of 9 scaled infrared absorption spectra. A horizontal line across each spectrum corresponds to its 4th-most intense scaled absorption intensity—it is the binary divider of the spectrum (FIG. 1). These nine binary fields, with noise added, were submitted to the network filter as test data sets. Noise is defined as reversing a percentage of negative bits in the binary field of each analyte. At 20% noise error, the network begins producing false identifications, and the deterioration is chaotic beyond this value. Testing the trained network is also performed with scaled, binary-coded, theoretical spectral predictions ($T^B$), and spectra measured by a TL sensor ($S^B$). Correct and incorrect identification percentages are computed by the inner product of training vector and network vector read directly from each neuron in the network output layer (analog outputs).

In Table 2, the summed A-symbol suggests a training set data block of nine compounds (with vector definitions) comprising the training io file with header information (comments on problem definition and network purpose, and quantity input and output PEs). Molecular descriptions of the analyte compounds and their training properties per data block are given in Table 1. Each block fills the computing capacity of a 32MB Random Access Memory (RAM), 50 MHz, 80486 PC machine executing DynaMind under the MS-DOS operating system, Version 5.0.

The first test was feed-forwarding the training exemplars $A^B$ back through the binary BEP-trained network. The network performed one of nine detections with an expected accuracy of 100% true predictions and 0% false identifications. The percentage value is an inner product computation of the analog nine-component response by the network output layer and the training set epoch vector for each of the nine contaminant compounds. (In feed-forwarding, the target output vector is programmed as an unknown; the network must select any of the nine analyte(s) possessing spectral content in the input exemplar, or reject all nine analyte compounds on completion of its pattern search.)

Figure 3A:
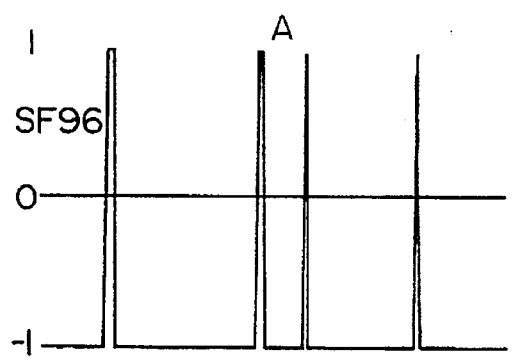
FIGS. 3A–3F show neural-network failure analyses.
Figure 3B:
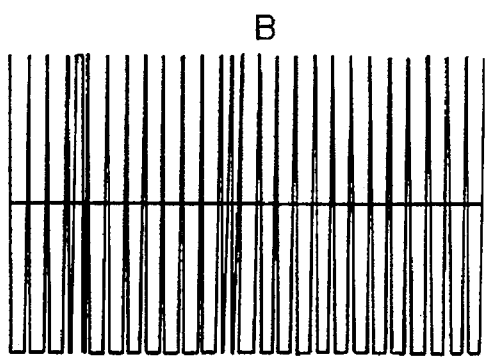
Figure 3C:
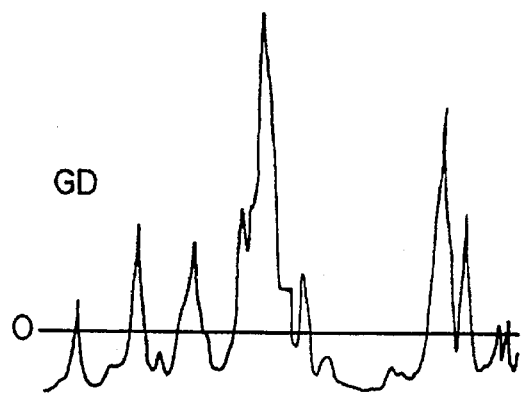
Figure 3D:
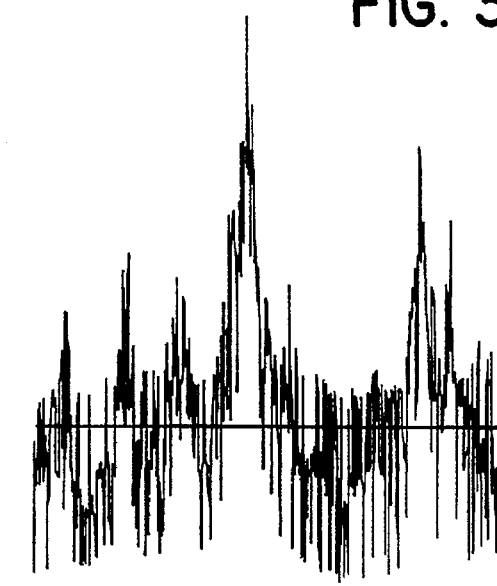
Figure 3E:
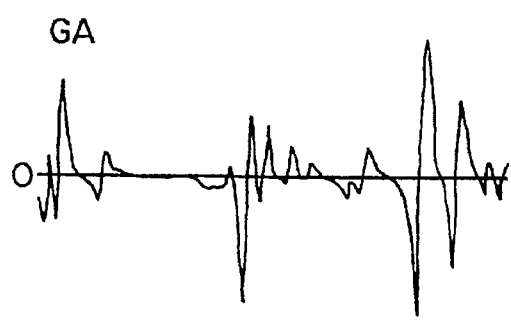
Figure 3F:
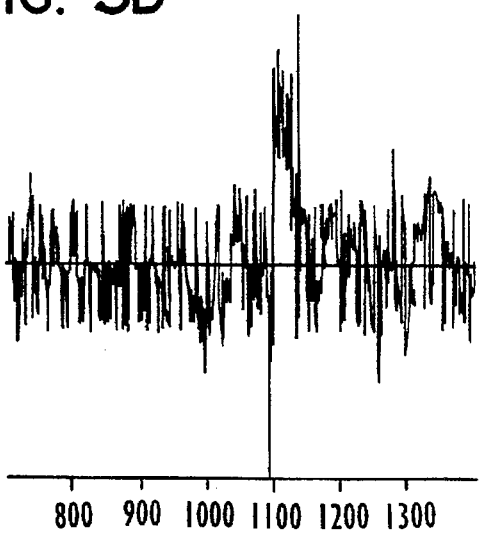

The next set of network performance tests was carried out with binary training data altered in a way to simulate noisy spectral data generated by an external sensor source. In this scheme, a percentage of negative (−1) bits in each exemplar of the data block representing all scaled analyte spectra was randomly reversed, then feed-forwarded it through the network. Pattern matching performance was excellent; this network weight matrix successfully filtered about 18% binary noise yielding accurate identifications of all nine contaminants. By adding 20% noise to the training data and feed-forwarding, the binary filter began breakdown by falsely detecting agent 5 (GB) in the agent simulant 8 (SF96) exemplar to 89.4%. The clean and noisy binary-encoded spectra of SF96 (exemplar 8) are graphed in FIGS. 3A and 3B.

To achieve the results shown in FIGS. 3A–3F, the inventors gradually increased noise in the training data set until the network failed to identify the analyte, until the network made incorrect identifications, or both failure modes were present. Column A (FIGS. 3A, 3C and 3E) is the analyte compound training data set plotted in: 4th-peak binary (top, SF96 ≡8), scaled decimal absorption (middle, GD≡6), and scaled decimal derivative-absorption (bottom, GA≡4) formats. (See Tab. 1) Column B (FIGS. 3B, 3D and 3F) shows the noise threshold for first network failure: 20% in B(SF96), 27% in B(GD) and 19% in B(GA). In B(SF96), the 4th-peak based binary filter identified two compounds: correct identification of SF96 to 98.7% certainty, and an incorrect identification of agent GB to 89.4% certainty. In B(GD), the absorption based filter also identified two compounds: a correct identification of agent GD to 98.7% certainty, and an incorrect identification of agent GF to 90.3% certainty. In B(GA) the derivative-absorption based filter failed to identify any of the 9 analyte compounds. (See Tabs. 2–3.) Noise above the tabulated values cause rapid deterioration in ability of these network filters to pattern-match one of nine compounds correctly.

Other absorption test data submitted to the network binary filter came from ab initio closed-shell molecular orbital (MO) calculations on each analyte molecule ($T^B$, $T^B$) by a popular program commonly used in quantum chemistry called Gaussian 92. A Hartree-Fock (HF) approximation was used with the 3–21G* wavefunction basis set option for producing these spectral predictions. The network is put to use as a system for checking validity of these quantum mechanics calculations against controlled experimental measurements (builders of the network filters). All spectral predictions by Gaussian were produced without knowledge of experimental data. Five of nine molecules, whose experimental spectra are ingrained in the binary filter, were initialized in Gaussian 92 format and successfully executed by the time of this writing: VX, DMMP, GA, GB, and GD, representing $T_0^B, T_3^B, T_4^B, T_5^B,$ and $T_6^B$; respectively. The VX calculation is superimposed on its experimental counterpart in FIG. 1.

Table 2 indicates an inability of the binary network filter to correctly pattern-match theory and experiment in all compounds except GD. Moreover, the GD correct detection event is shared with a false identification of G-agent simulant DIMP. These results suggest that accuracy of the calculation of vibrational energies and intensity of these energy transitions in molecules the size of VX (and higher molecular weight) is critical.

The third and most important test of these binary network filters comes from forwarding of data generated by a prototype TL sensor ($S^B$). These raw sensor data were derived from the difference of two slightly shifted graybody spectra measured during irradiation by a laser source beam emitting at 829 cm$^{-1}$. It was necessary to block all scattered laser light from entering the interferometer by inserting a cutoff CaF window in the entrance aperture just before the interferometer beamsplitter. The CaF crystal did block the laser scattering energy, but it also caused attenuation of TL collected between 700 to about 900 cm$^{-1}$. (The CaF bandpass cutoff was not as sharp as desired.) The other anomaly of these sensor spectra are their 4 cm$^{-1}$ resolution—twice less resolved than the spectra used to create the network binary filter. (Both of these problems are remedied in a new system with improved two-wavenumber interferometer and microwave TL stimulator.)

The sensor data inputs to these networks were produced from the inventors' work on TL detection of liquid layers and evaporated vapors of organics DIMP ($S_2^B$), DMMP ($S_2^B$) and SF96 ($S_8^B$) wetting various terrains. The results in Table 2 show that the binary neural filter detected one of nine analyte compounds accurately with no false detections. This is indeed a remarkable achievement given the senor data are low resolution and truncated in the lower IR band of the measuring instrument. Currently, the inventors are restructuring the binary (and decimal) filters for any of N analyte detections. The training data will require known absorption cross-sections for each major vibrational resonance in all analyte compounds, viz, quantitative data are required for creating exemplars of mixed compounds. The training data block will now consist of $2^N-1$ exemplars, N limited by available computer RAM memory.

Table 3 below lists performance results on the same network architecture used to build the binary filter, except now it is trained against pre-processed IR decimal absorption (page 19 of Table, $A^D$) and first-derivative absorption (page 20 of Table, $A^D$) analyte spectra. The inventors added a rule in the decision columns: reject identification by the filters, correct or incorrect, below a 90% confidence limit.

TABLE 3

| | Decimal Data Set Representation | | | |
|---|---|---|---|---|
| Training Spectrum | Testing Spectrum | Added Noise (%) | Correct ID >90% Agent (% True) | Incorrect ID >90% Agent (% False) |
| $\sum_{i=0}^{8} A_i^D$ | $A_0^D, A_1^D, A_2^D$ $A_3^D, A_4^D, A_5^D$ $A_6^D, A_7^D, A_8^D$ | 25 | 0(98.7), 1(98.7), 2(98.7) 3(98.7), 4(98.7), 5(98.7) 6(98.7), 7(98.7), 8(98.7) | None None None |
| | $A_0^D, A_1^D, A_2^D$ $A_3^D, A_4^D, A_5^D$ $A_6^D, A_7^D, A_8^D$ | 27 | 0(98.7), 1(98.7), 2(98.7) 3(98.7), 4(98.7), 5(98.7) 6(98.7), 7(98.7), 8(98.7) | None None 6→7(90.3) |
| $\sum_{i=0}^{8} A_i^D$ | $T_0^D$ $T_3^D$ $T_4^D$ | 0 | No ID 3(98.7) 4(98.7) | 7(98.7) None 1(98.7), 3(98.7), 6(92.9), 7(98.4) |
| | $T_5^D$ $T_6^D$ | | No ID 6(98.7) | 2(91.4), 7(98.7) 2(98.7), 7(98.7) |
| $\sum_{i=0}^{8} A_i^D$ | $S_2^D$ $S_3^D$ $S_8^D$ | 0 | 2(98.7) 3(98.7) 8(98.7) | None None None |

Transfer Function Gain = 1.50, Learning Rate = 0.120

| | | | | |
|---|---|---|---|---|
| $\sum_{i=0}^{8} \dot{A}_i^D$ | $\dot{A}_0^D, \dot{A}_1^D, \dot{A}_2^D$ $\dot{A}_3^D, \dot{A}_4^D, \dot{A}_5^D$ $\dot{A}_6^D, \dot{A}_7^D, \dot{A}_8^D$ | 13 | 0(98.7), 1(98.7), 2(98.7) 3(98.7), 4(98.7), 5(98.7) 6(98.7), 7(98.7), 8(98.7) | None None None |
| | $\dot{A}_0^D, \dot{A}_1^D, \dot{A}_2^D$ $\dot{A}_3^D, \dot{A}_4^D, \dot{A}_5^D$ $\dot{A}_6^D, \dot{A}_7^D, \dot{A}_8^D$ | 19 | 0(98.7), 1(98.7), 2(98.7) 3(98.7), 4(No ID), 5(98.7) 6(98.7), 7(98.7), 8(98.7) | None None None |
| $\sum_{i=0}^{8} \dot{A}_i^D$ | $\dot{T}_0^D$ | 0 | No ID | 3(98.7), 5(98.7), 6(98.7) |
| | $\dot{T}_3^D$ | | No ID | 1(97.5), 5(98.7), |

TABLE 3-continued

Decimal Data Set Representation

| Training Spectrum | Testing Spectrum | Added Noise (%) | Correct ID >90% Agent (% True) | Incorrect ID >90% Agent (% False) |
|---|---|---|---|---|
| | | | | 8(98.6) |
| | $T_4^D$ | | No ID | None |
| | $T_5^D$ | | No ID | None |
| | $T_6^D$ | | No ID | None |
| $\sum_{i=0}^{8} A_i^D$ | $S_2^D$ | 0 | — | — |
| | $S_3^D$ | | — | — |
| | $S_8^D$ | | — | — |

Transfer Function Gain = 1.00, Learning Rate = 0.200

Input layer neurons = 350, 1st hidden layer neurons = 256 and 2nd hidden layer neurons = 128, output layer neurons = 9, epoch error < $10^{-15}$, weight limits ±2.5, $A^D$ = decimal IR absorption spectrum, (Nicolet MX-1 or 10-DX spectrometer measurement), $\dot{A}^D$ = decimal first derivative absorption spectrum, i = (0, 1, 2, 3, 4, 5, 6, 7, 8) ≡ (VX, Vx, DIMP, DMMP, GA, GB, GD, GF, SF96), $T^D$ = decimal Gaussian 90 model theoretical prediction spectrum, $\dot{T}^D$ = decimal first derivative theoretical prediction absorption spectrum, $S^D$ = decimal interferometer sensor spectrum, $\dot{S}^B$ = decimal first derivative interferometer sensor spectrum.

Given in Table 3 above are network neurons per input-hidden-output layers, converged epoch error, and tanh transfer function parameters including gain and learning rate. The summed A-symbol suggests a decimal format of nine scaled infrared absorption spectra (page 19) and its first-derivative (page 20). With the addition of noise to each spectrum, these training data sets were re-submitted as test data sets of the trained network filters. Noise is defined as a random percentage of the most intense peak (seed) value in each spectrum of the training set; it is added or subtracted point-by-point to all training set spectra. Noise above the tabulated set; values cause chaos or confusion by the network to provide accurate target decisions. Testing the trained network is also performed with passage of scaled decimal data representing theoretical predictions of absorption spectra and its computed first derivative spectra ($T^D$, $\dot{T}^D$), and spectra measured by a TL sensor system ($S^D$, $\dot{S}^D$). Correct and incorrect identification percentages are computed by the inner product of training vector and network output vector. Results of correct or incorrect identifications use a 90% cutoff rule. The dashed entries infer unsuccessful preparation (preprocessing) of raw spectra for network submittal.

The network performance results for noisy training data between straight absorption and derivative-absorption trained networks show resemblance. Network performance between binary and decimal based networks cannot be compared by virtue of different definitions of noise. In the decimal networks, the scaled absorption peak intensity in each analyte exemplar was first located. The noise percentage value given in Table 3 is a percentage of this peak value. A random number generator used this peak value as an upper bound per spectrum for distributing extraneous signal to each training exemplar (point-by-point random additions and subtractions, or no change). In the absorption decimal filter, 27% noise in the training data sets cause initial network breakdown; here a first false identification of agent GF(7) in agent exemplar GD(6) is shown. The derivative-absorption decimal filter began showing problems of true decision making at 19% noise, where it failed to identify agent GA(4).

Performance by these filters from feed-forwarding decimal theoretical spectra ($T^D$, $\dot{T}^D$) are next shown in Table 3. As with its binary filter counterpart, performance results are not good for these decimal filters. Table 3 shows that true identification with no false positives was made only once with submission of the theoretical DMMP absorption decimal spectrum. All other results show true identifications shared with false positives, null true decisions, or null true decisions with false positives. The conclusion here is the same as with the binary filter tests: Theoretical spectra cannot substitute for experimental spectra when training these network filters for successful detection of agents given the level of theory used or the methods of Gaussian 92 computations performed. Better agreement of analyte IR absorption frequencies and intensity of absorptions is required between experiment and theory. The accuracy of spectral prediction can be much improved by new and better methods of computation.

Network filtering of the decimal sensor spectra ($S^D$, $\dot{S}^D$) is the next group of results in Table 3. Again, these data lack resolution and have inherent truncated TL signal in the lower spectral band of the FTIR instrument. The decimal absorption network filter results are remarkably accurate and reproducible: all true positives and no false positives with high confidence. Performance results by the derivative-based network filter are not shown because of major shortcomings in preprocessing of these differentiated field sensor spectra. As previously noted, derivative data require high resolution and special smoothing techniques in preprocessing. The derivative-absorption based neural filter will be retested when better sensor data become available.

Figure 4:
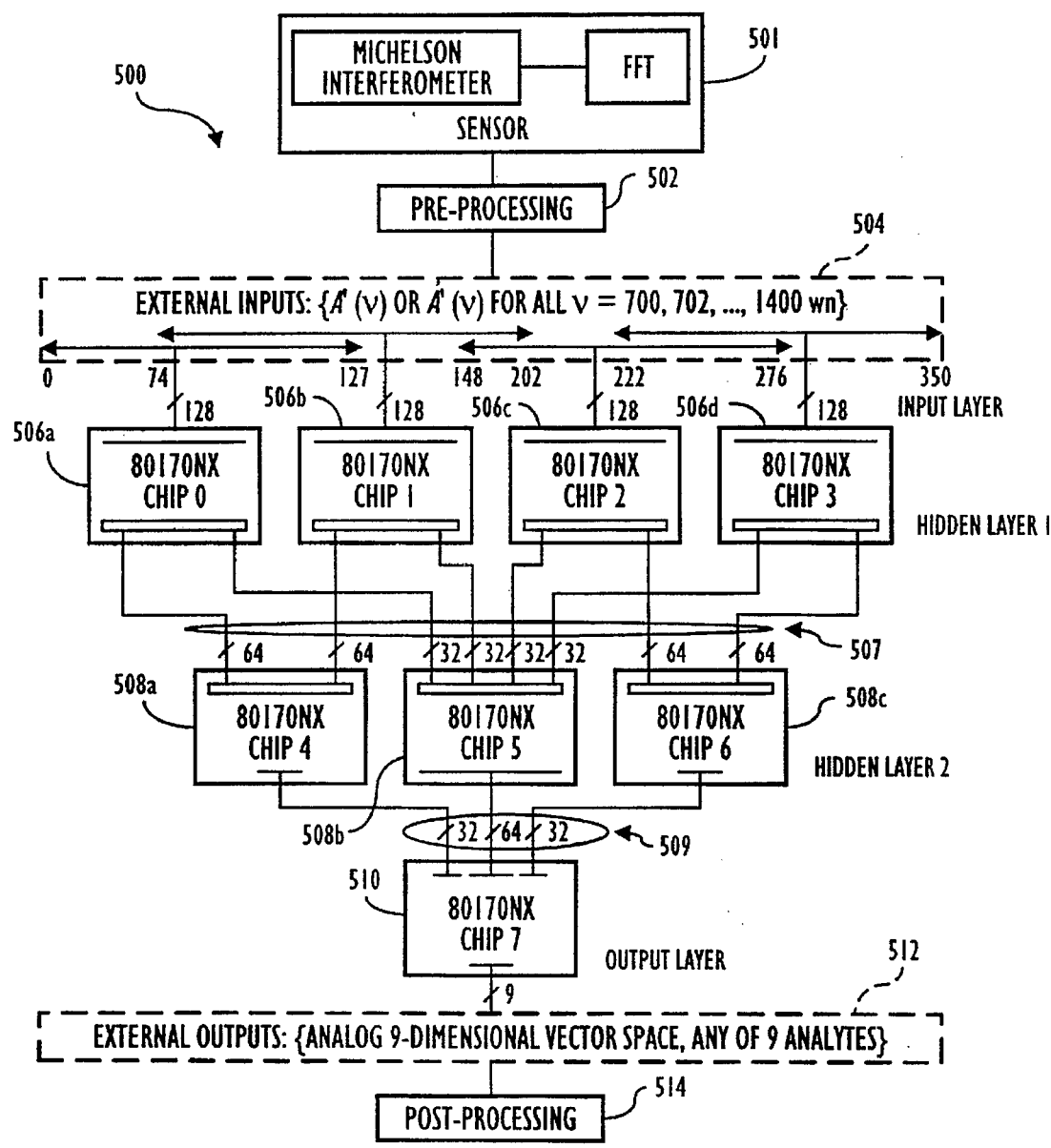
FIG. 4 shows a diagram of hardware used in the present invention.

FIG. 4 depicts a neural network implemented in hardware 500, with chip layout and procedure for downloading these network architectures and learned weight matrices to the Intel IC hardware. Also shown in sensor 501 with Michelson interferometric and an FFT module. Transferral to high-speed neural chips is necessary for employing these NNCs as real-time sensor decision-makers. (Real-time can be better stated as the minimum time of throughput from collection of radiance to post-processing of the network output layer data.) Spectral pattern-matching and decision making tasks are done in short order by design of the 80170NX neural chip, firmware housing (EMB board), and the software drivers that control communications in a group of eight chips; computational throughputs exceed $16 \times 10^9$ PE interconnections per second. (Scan rate of the Michelson interferometer mirror is the bottleneck in arriving at a detection decision from the NNC system.)

The modular architecture of FIG. 4 is a manifestation of how DynaMind translates the network filters into 80170NX IC hardware. All chips 506a ... 510 are initialized to 128 input PEs. Chips 506a–506d cover the midinfrared spectrum in overlapping groups of 128 PEs, 350 independent TL spectral amplitudes passed on from the sensor's DSP array pre-processing board 502 through input layer 504. The succeeding three neural chips 508a–508c accept output from the first hidden layer of 256 PEs. Between hidden layers are eight modules 507 of the network architecture. Hidden layer 2 with chips 508a–508c produces 128 outputs distributed to chip 510: here there are 3 network modules 509. The final module is the network output 512 of nine PEs. This final module represents a nine-dimensional decision vector whose nine analog signal components are sent to post-processing modules 514 that make event and non-event decisions. These no alarm/alarm events are later used in localized coordinate mapping functions, part of the sensor post-processing tasks. These mappings include the display of terrain maps, with tracking of alarm icons, routed to electronics ground stations using a Global Positioning System. Other functions related to systems automation, signal processing, and safe operation of the sensor will be documented later. The configuration file required by DynaMind for chip transferral of these four-layer binary and decimal formatted networks reads thus:

quality. Performance by the decimal derivative-absorption filter from our preprocessing treatments of these sensor data is lacking and inaccurate. The problems of poor performance encountered with the derivative-based sensor spectra can be improved with better instrument hardware (new TL stimulation source, and better instrument resolution) and preprocessing algorithms (better smoothing operation).

Training periods by the four-layer network with binary encoded data are inherently shorter than with a decimal format. However, in the one of nine problem, network feed-forwarding time frames (interval from submission of spectra to the network input layer to output layer result, in ms) are similar for all data formats by chip-in-loop hardware implementation. The any of N problem can be solved by binary filter using a cascading data procedure. The same problem with decimal-based filters can be solved by retraining the networks with quantitative absorption analyte spectra, $2^N-1$ exemplars. The latter network filter would yield detection decisions quicker. For implementing the decimal filters, complications from adding a bank of D/A converters to the data acquisition system is realized.

With these factors in mind, the neural network filter built with the binary format structure is best suited for the one of nine 9 TL spectral pattern recognition problem. There is room for improvement of network design. False detections by noise in the sensor exceeding those limits established in

```
* CFG file for pattern recognition of 9           Chip1Out[0..31]-Chip4In[64..95]
agents                                            Chip1Out[32..63]-Chip4In[96..127]
* 8 chip, 4-layer, back-prop nn to solve the      Chip1Out[0..31]-Chip5In[32..63]
*binary 4th peak detection problem                Chip2Out[0..31]=Chip5In[64..95]
* IO File: a4pkb.io                               * Next line split into two weight matrices
* Number of Inputs                                Chip2Out[0..31]-Chip6In[0..31]
INPUT 350 * 350 inputs over 4 chips: 0-3          Chip2Out[32..63]-Chip6In[32..63]
* Number of Outputs                               Chip3Out[0..31]-Chip5In[96..127]
OUTPUT 9 * 9 outputs from chip 7                  * Next line split into two weight matrices
* From sensor preprocessing                       Chip3Out[0..31]-Chip6In[64..95]
Layer 1 * Sensor IR spectral data, 350 PEs        Chip3Out[32..63]-Chip6In[96..127]
ExternalIn[0..127]-Chip0In[0..127]                Layer 3 * Second hidden layer, 128 PEs
ExternalIn[74..201]-Chip1In[0..127]               Chip4Out[0..31]-Chip7In[0..31]
ExternalIn[148..275]-Chip2In[0..127]              Chip5Out[0..63]-Chip7In[32..95]
ExternalIn[222..349]-Chip3In[0..127]                                         In[96...127]
Layer 2 * First hidden layer, 256 PEs             ExtLayer * "any of 9 analytes" space, 9
* Next 2 lines split weight matrices              PEs
Chip0Out[0..31]-Chip4In[0..31]                    Chip7Out[0..8]-ExternalOut[0..8]
Chip0Out[32..63]-Chip4In[32..63]                  * To sensor post-processing
Chip0Out[0..31]-Chip5In[0.31]
* Next 2 lines split weight matrices
```

Figure 5:
FIG. 5 shows a training procedure used in the present invention.

FIG. 5 shows an overview of the training directed above.

Binary and decimal based neural network filters built from molecular absorption by nine contaminant compounds were presented. These network filters set accurate performance standards by results of tests using spectral data with large spurious noise content and/or from spectra with low resolution and partly attenuated bandwidth. Improved algorithms for the preprocessing of raw spectral data, in situ, especially for the decimal derivative-absorptic, in format of difference spectra, are being investigated.

No strong advantage is seen in filtering performance by these networks between submissions of respective binary absorption and decimal absorption data formats, with noise, in solving the one of nine contaminant problem. Furthermore, no advantage in filter performance is shown between decimal absorption and its derivative format of 1 cm$^{-1}$ resolved laboratory spectra. True and accurate results by the straight decimal absorption filter and the binary filter were realized from submission of sensor data. These results are reproducible, given the sensor data are not of the highest Tables 2 and 3 could be costly: network training by the gradient descent paradigm does not penalize false positive or false negative decisions. For establishing better confidence of spectral detection, these analyses can be extended to Radial Basis Function (RBF) networks. RBF networks are a forward, 3-layer, architecture where summation and activation function units in the hidden layer combine to form radial basis functions. The decision boundary by RBF training is rounded in dimensional weight space with radius and center point. In training, these networks can be made to deactivate hidden layer PEs that contribute to a false identification and make active those hidden layer PEs that are suppressed in positive non-decision events. NNC hardware implementation of these IR spectral filters is possible with Intel Corporation's Ni1000 IC chip, a neural network product based on the RBF.

Thermoluminescence in natural and manufactured materials is investigated and applied to a standoff sensor concept where:

(a) rate of change of liberated TL flux is generated by beam irradiation whose energy is strongly absorbed by the surface and coupled into the volume.

(b) A major part of the absorbed energy drives rotational states in water molecules that cause heating of the neighborhood medium, developing in it a temperature gradient between unlike materials.

(c) TL radiance liberated from this temperature non-equilibrium zone are collected within the 8–12 micrometer wavelength band by a telescope, collimated, passed through a Michelson interferometer, then spectrally deconvolved into thermal signature spectra. This is done when the temperature gradient in the beam irradiation zone is maximum, producing maximum contrast of emissivity between target(s) (vibrationally active molecules to be detected) and background. (bulk matrix).

(d) In this thermal window, contiguous sets of transformed interferograms are subtracted, corrected for base-line drift, scaled, filtered, and cast into binary or decimal data formats for (e) pattern recognition by a highly tuned neural network filter.

The neural network seeks-out molecular vibrational properties in the stimulated contaminant within this window of thermal opportunity. If vibrational features are brought-out in the network output layer, with high confidence, then a positive condition is set and electronically routed for post-processing and advance warning.

This disclosure sets forth a preferred embodiment of the invention. However, those skilled in the art who have reviewed this disclosure will readily appreciate that other embodiments within the scope of the invention are possible. For example, different software and microprocessor chips could be used. Therefore, the invention should be construed as limited not by the preferred embodiment, but only by the appended claims.

We claim:

1. A system for recognizing compositions of matter in accordance with thermoluminescence exhibited by the compositions of matter, the system comprising:

sensor means for detecting the thermoluminescence; spectral analysis means for analyzing the thermoluminscence detected by the sensor means to produce spectral data for a plurality of wave numbers; and artificial neural network means for receiving the spectral data and for determining, in accordance with the spectral data, whether the thermoluminescence detected by the sensor means indicates the presence of the compositions of matter.

2. A system as in claim 1, wherein the spectral data are binary data.

3. A system as in claim 1, wherein the spectral data are decimal data.

4. A system as in claim 1, wherein:

the spectral data comprise a plurality of discrete spectral data; and the artificial neural network means comprises one input neuron for each of the plurality of discrete spectral data.

5. A system as in claim 4, wherein the artificial neural network means further comprises one output neuron for each of the plurality of compositions of matter to be recognized.

6. A system as in claim 5, wherein the artificial neural network means further comprises first and second hidden layers.

7. A system as in claim 6, wherein:

the input layer has 350 neurons;

the first hidden layer has 256 neurons; and the second hidden layer has 128 neurons.

8. A system as in claim 7, wherein the output layer has nine neurons.

9. A system as in claim 8, wherein the artificial neural network means comprises:

a plurality of artificial neural network chips, each comprising a plurality of neurons; and motherboard-bus means for interconnecting the plurality of artificial neural network chips in a serial-parallel configuration to provide the input layer, the first and second hidden layers and the output layer.

10. A system as in claim 1, wherein the sensor means comprises:

a Michelsen interferometer for producing raw data; and fast Fourier transform means for converting the raw data into data indicating the thermoluminescence.

11. A method of training an artificial neural network to recognize compositions of matter in accordance with thermoluminescence exhibited by the compositions of matter, the method comprising:

(a) providing known absorption spectra for the compositions of matter;

(b) differentiating the known absorption spectra with respect to absorption time to derive differentiated absorption spectra; and (c) training the artificial neural network by backward error propagation with the known absorption spectra and the differentiated absorption spectra to obtain a plurality of neural network weights for the artificial neural network.

12. A method as in claim 11, further comprising:

(d) providing a second artificial neural network having a same configuration of neurons as the artificial neural network; and (e) exporting the plurality of neural network weights from the artificial neural network to the second artificial neural network;

whereby the second artificial neural network becomes capable of recognizing the compositions of matter.

13. A method as in claim 11, wherein step (c) comprises converting the known absorption spectra into binary values and supplying the binary values to the artificial neural network.

14. A method as in claim 11, wherein:

step (c) comprises converting the spectral data into a plurality of discrete spectral data; and the artificial neural network comprises one input neuron for each of the plurality of: discrete spectral data.

15. A method as in claim 14, wherein the artificial neural network further comprises one output neuron for each of the compositions of matter to be recognized.

16. A method as in claim 15, wherein the artificial neural network means further comprises first and second hidden layers.

17. A method as in claim 16, wherein:

the input layer has 350 neurons;

the first hidden layer has 256 neurons; and the second hidden layer has 128 neurons.

18. A method as in claim 17, wherein the output layer has nine neurons.

19. A method as in claim 11, wherein step (c) comprises converting the known absorption spectra into decimal values and supplying the decimal values to the artificial neural network.

* * * * *